(12) United States Patent
Okuno et al.

(10) Patent No.: US 6,344,568 B1
(45) Date of Patent: Feb. 5, 2002

(54) CATALYST FOR GAS PHASE PARTIAL OXIDATION

(75) Inventors: Masaaki Okuno; Hiromi Yunoki; Yasushi Kiyooka; Daisuke Nakamura; Michio Tanimoto; Tsukasa Takahashi, all of Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/378,148

(22) Filed: Aug. 20, 1999

(30) Foreign Application Priority Data

Feb. 19, 1999 (JP) ............................................. 11-041917
Jun. 24, 1999 (JP) ............................................. 11-178785

(51) Int. Cl.⁷ .................... C07D 307/33; C07D 307/89; C07C 27/14; C07C 51/215; C07C 51/265
(52) U.S. Cl. ........................ 549/248; 549/256; 549/262; 558/303; 558/309; 562/409; 562/494; 562/512.2
(58) Field of Search ................................. 549/303, 313, 549/248, 256, 262; 558/303, 309; 562/512.2, 533, 535, 409.7, 494

(56) References Cited

U.S. PATENT DOCUMENTS

| | | | |
|---|---|---|---|
| 3,773,692 A | 11/1973 | Hensel et al. | 252/455 R |
| 3,867,438 A | 2/1975 | Hensel et al. | 260/530 N |
| 4,014,925 A | 3/1977 | Ferlazzo et al. | |
| 4,414,412 A | 11/1983 | DeAlberti et al. | 562/535 |
| 4,665,200 A | 5/1987 | Nakanishi et al. | 549/239 |
| 4,760,153 A | 7/1988 | Takahashi et al. | 549/257 |
| 4,939,260 A | 7/1990 | Inoue et al. | 546/286 |

FOREIGN PATENT DOCUMENTS

| | | | |
|---|---|---|---|
| DE | 2235103 | 2/1974 | |
| GB | 1 468 005 | 3/1977 | ............ C07C/57/04 |
| GB | 1 488 889 | 10/1977 | ............ B01J/23/28 |
| GB | 1 488 890 | 10/1977 | ............ B01J/23/28 |
| HU | 32265 | 9/1984 | |
| JP | 50-25914 | 8/1975 | ............ B01J/23/28 |
| JP | 50022994 | 8/1975 | |
| JP | 57-105241 | 6/1982 | ............ B01J/27/18 |
| JP | 58159849 | 9/1983 | |
| JP | 9-85096 | 3/1997 | .......... B01J/27/224 |
| SU | 1377138 | 2/1988 | |

Primary Examiner—T. A. Solola
(74) Attorney, Agent, or Firm—Fish & Richardson PC

(57) ABSTRACT

This invention relates to a method for producing a partially oxidized organic compound, e.g., an unsaturated aldehyde/carboxylic acid having three or more carbon atoms, or an organic acid anhydride/nitrile compound having four or more carbon atoms. This method requires a catalyst prepared by treating a carrier in such a manner that water used in the treatment achieves specific resistance.

7 Claims, No Drawings

CATALYST FOR GAS PHASE PARTIAL OXIDATION

BACKGROUND OF THE INVENTION

1. Field of the Invention

This invention relates to a catalyst for the gas phase partial oxidation of an organic substrate, a method for the preparation thereof, and a method for producing a partially oxidized organic compound using the catalyst.

2. Description of the Related Art

For the production of acrylic acid, it has been widely practiced on a commercial scale a method which adopts acrolein as a raw material and effects gas phase partial oxidation thereof with molecular oxygen in the presence of a catalyst. In the catalysts for use in this production of acrylic acid, the catalysts are mainly used which have molybdenum-vanadium as a main component. Patents which have issued to inventions covering molybdenum-vanadium type catalysts include those disclosed in JP-B-50-25,914, GB 1 488 889, GB 1 488 890, U.S. Pat. Nos. 3,773,692, 3,867,438, 4,414,412 etc.

While these catalysts for the production of acrylic acid have already reached the point where they exhibit yields of high levels, they are still required to offer further improved yields. The reason for this is that since acrylic acid is now produced on a large scale, even a slight improvement of yield brings a very high economic effect due to economization of raw material. Further, the improvement of such a catalyst in service life and durability brings about an extremely large economic effect.

Owing to this situation, the development of a catalyst for the production of acrylic acid which excels in catalytic qualities such as activity, selectivity, and service life constitutes a constant theme for researchers in the relevant technical field.

The gas phase partial oxidation of aromatic compounds or alkyl-substituted heterocyclic compounds are practiced widely on a commercial scale, such as the production of phthalic anhydride by the gas phase partial oxidation of orthoxylene and/or naphthalene, the production of maleic anhydride by the gas phase partial oxidation of benzene, the production of pyromellitic anhydride by the gas phase partial oxidation of 1,2,4,5-tetraalkyl benzene, and the production of an aromatic nitrile or a heterocyclic nitrile by the ammoxidation of an alkyl-substituted aromatic compound or an alkyl-substituted heterocyclic compound. Various catalysts have been proposed for use in the gas phase partial oxidation.

These gas phase partial oxidation catalysts have excellent properties of themselves. Nevertheless, the development of gas phase catalysts excelling in catalytic qualities such as activity, selectivity, and service life constitutes a constant theme for researchers in the relevant technical field.

SUMMARY OF THE INVENTION

An object of this invention is to provide a catalyst for the gas phase partial oxidation of an organic substrate which excels in catalytic qualities and enables the target product to be obtained stably in a high yield for a long time.

Another object of this invention is to provide a method for producing a partially oxidized organic compound by the use of the catalyst.

Yet another object of this invention is to provide a method of preparation suitable for the preparation of the catalyst.

According to the first embodiment of this invention, it provides a catalyst for the gas phase partial oxidation of an organic substrate which comprising a catalytically active component supported on an inert carrier, the carrier having at least one property selected from the group consisting of the water after the following treatment exhibits specific resistance of not less than 10,000 $\Omega$.cm (25° C.) in the case of producing an unsaturated aldehyde or an unsaturated carboxylic acid having not less than three carbon atoms and containing at least one double bond, and the water after the following treatment exhibits specific resistance of not less than 20,000 $\Omega$.cm (25° C.) in the case of producing an organic acid anhydride or a nitrile compound having not less than four carbon atoms:

(Method of Treatment)

In a conical beaker having an inner volume of 500 ml, 300 ml of a given carrier is placed and dried at 120° C. for two hours and then the dried carrier and (amount of water absorption+220) ml of purified water added thereto are heated at 90° C. under normal pressure for 30 minutes, wherein the amount of water absorption is represented as follows:

$$\text{Amount of water absorption} = A/B$$

wherein $A = 300$ (ml)×packing density (g/ml)×water absorption ratio (wt. %)/100 and $B =$ density of water (g/ml).

According to the second embodiment of this invention, it provides a method for the production of a partially oxidized organic compound which comprises effecting gas phase partial oxidation of an organic substrate or an organic substrate-containing gas with a molecular oxygen or a molecular oxygen-containing gas in the presence of the catalyst mentioned above.

Further, according to the third embodiment of this invention, it provides a method for the preparation of a catalyst for the gas phase partial oxidation of an organic substrate, which comprises supporting a catalytically active component on an inert carrier, the carrier having at least one property selected from the group consisting of the water after the following treatment exhibits specific resistance of not less than 10,000 $\Omega$.cm (25° C.) in the case of producing an unsaturated aldehyde or an unsaturated carboxylic acid having not less than three carbon atoms and containing at least one double bond, and the water after the following treatment exhibits specific resistance of not less than 20,000 $\Omega$.cm (25° C.) in the case of producing an organic acid anhydride or a nitrile compound having not less than four carbon atoms:

(Method of Treatment)

In a conical beaker having an inner volume of 500 ml, 300 ml of a given carrier is placed and dried at 120° C. for two hours and then the dried carrier and (amount of water absorption+220) ml of purified water added thereto are heated at 90° C. under normal pressure for 30 minutes, wherein the amount of water absorption is represented as follows:

$$\text{Amount of water absorption} = A/B$$

wherein $A = 300$ (ml)×packing density (g/ml)×water absorption ratio (wt. %)/100 and $B =$ density of water (g/ml).

The catalyst for the production of a partially oxidized organic compound according to this invention excels in activity, selectivity, and service life and enables the partially oxidized organic compound to be produced in a high yield for a long time.

The above and other objects, features, and advantages of the present invention will become clear from the following description of the preferred embodiments.

DESCRIPTION OF THE PREFERRED EMBODIMENTS

As examples of the partially oxidized organic compound to be obtained by the use of the gas phase partial oxidation catalyst of this invention, it may be cited an unsaturated aldehyde or an unsaturated carboxylic acid having not less than three carbon atoms and an organic acid anhydride or a nitrile compounds having not less than four carbon atoms. The unsaturated aldehyde or unsaturated carboxylic acid includes those having three–five carbon atoms, more preferably (meth)acrolein and (meth)acrylic acid. The organic acid anhydride or nitrile compounds include aromatic acid anhydride compounds, aromatic nitrile compounds and heterocyclic nitrile compounds, preferably organic acid anhydride, aromatic nitrile and heterocyclic nitrile having four–ten carbon atoms, and more preferably phthalic anhydride, maleic anhydride, pyromellitic anhydride, benzonitrile, picolino-nitrile etc.

The treatment to be used in this invention prior to the determination of the specific resistance of water is performed by the following method: In a conical beaker having an inner volume of 500 ml (based on Japanese Industrial Standard (JIS) R-3503), 300 ml of a given carrier is placed and dried at 120° C. for two hours and then the dried carrier and (amount of water absorption+220) ml of purified water added thereto are heated at 90° C. under normal pressure for 30 minutes, wherein the amount of water absorption is represented as follows:

Amount of water absorption=A/B wherein
A=300 (ml)×packing density (g/ml)×water absorption ratio (wt. %)/100 and
B=density of water (g/ml).

The term "packing density (D)" used in the preceding formula means the magnitude which is represented by the formula, D=W1 (g) /1000 ml (wherein W1 denotes the weight of the carrier which fills a measuring cylinder, 65 mm in inside diameter 1000 ml in inner volume, when the dried carrier is fed into the measuring cylinder at a rate of 2000 ml/minute).

The term "water absorption ratio (M)" used therein means the magnitude which is represented by the formula, M=[(W3 (g)–W2 (g) )/W2 (g)] (wherein W2 denotes the weight of 300 ml of the dried carrier and W3 denotes the weight found after 300 ml of the dried carrier is placed in a basket made of stainless steel wire, heated in boiling purified water for 30 minutes, then removed from the basket, wiped with a wet gauze till removal of excess water, and weighed).

The following description is based on (I) acrylic acid as a typical example of the partial oxidized aliphatic compounds mentioned above and (II) phthalic anhydride, maleic anhydride, pyromellitic anhydride, aromatic nitrile, and heterocyclic nitrile as typical examples of the organic acid anhydride or nitrile compounds mentioned above.

(I) Partial Oxidized Aliphatic Compounds

Specifically, this invention includes a catalyst for the production of acrylic acid which comprising the oxide or complex oxide of a metal element composition having molybdenum and vanadium as main components thereof and a inert carrier on which the metal element composition is supported, characterized by the carrier used therein causing the water after undergoing the treatment mentioned above to exhibit specific resistance of not less than 10,000 $\Omega$.cm (25° C.).

The carrier to be used in this invention does not need to discriminate the material therefor. It can be used in preparing an oxidizing catalyst for the production of acrylic acid by the gas phase partial oxidation of acrolein or an acrolein-containing gas and can use any of materials which are popularly known as usable for the production. As examples of the material widely used for the carrier of catalyst,it may be cited alumina, silica, silica.alumina, titania, magnesia, silica.magnesia, silica.magnesia.alumina, silicon carbide, silicon nitride, and zeolite, and preferably silica.alumina, silica.magnesia.alumina, silicon carbide.

The carrier is not particularly discriminated on account of physical properties, shape, size etc. As respects physical properties, the specific surface area thereof is not more than 2 $m^2$/g and preferred to be in the range of 0.01–1.5 $m^2$/g, the water absorption ratio thereof in the range of 0–70%, preferably 0–50%, and the average pore diameter thereof in the range of 1–1,500 $\mu$m, preferably 5–500 $\mu$m. The shape may be arbitrarily selected from among sphere, cylinder, hollow cylinder etc. The size is in the range of 1–10 mm, preferably 3–8 mm, in diameter in the case of spheres.

This invention is characterized by using a carrier which causes the water after undergoing the treatment mentioned above to exhibit specific resistance of not less than 10,000 $\Omega$.cm (25° C.). Specifically, the carrier to be used is such that when 300 ml of the carrier is placed in a conical beaker having an inner volume of 500 ml and dried at 120° C. for two hours, and then the dried carrier and (amount of water absorption+220) ml of purified water added thereto are heated at 90° C. under normal pressure for 30 minutes, the water subsequently to this treatment exhibits specific resistance not less than $1 \times 10^4$ $\Omega$.cm (25° C.), preferably falling in the range of 15,000–$1 \times 10^6$ $\Omega$.cm (25° C.), and particularly preferably falling in the range of $2 \times 10^4 \times 1$–$10^6$ $\Omega$.cm (°C.).

The term "specific resistance" herein refers to the magnitude which is the reciprocal of the conductivity of water determined after the treatment mentioned above at 25° C. by the use of a conductivity meter. In this invention, when the specific resistance is 10,000 $\Omega$.cm, for example, it is expressed as 10,000 $\Omega$.cm (25° C.).

The carrier which exhibits the specific resistance of not less than 10,000 $\Omega$.cm (25° C.) for the water after the treatment mentioned above can be advantageously prepared by washing a given carrier with water, preferably purified water, to a certain level.

One concrete method for effecting this washing consists in that the specific resistance for the water after the treatment mentioned above exceeds $1 \times 10^4$ $\Omega$.cm (25° C.), preferably falls in the range of 15,000 to $1 \times 10^6$ $\Omega$.cm (25° C.), and more preferably 20,000–$1 \times 10^6$ $\Omega$.cm (25° C.), for example by repeating an operation of heating a carrier under normal pressure at 90° C. for 30 minutes. This operation does not need to be repeated when the first round of the operation allows the specific resistance for the water after the treatment mentioned above reaches a level exceeding 10,000 $\Omega$.cm (25° C.). When the operation is performed a plurality of times, each operation must use newly supplied water and require this water to be tested for specific resistance subsequently to the treatment mentioned above. The amount of water to be used for the washing does not need to be particularly limited. When the carrier has a volume of 300 ml, for example, the amount of water to be used is the sum of amount of water absorption and 220 ml in the first round of the operation and 220 ml each in the second and subsequent rounds. This is because the treated carrier contains the water corresponding to the amount of water absorption.

Prior to the washing with water described above, the carrier may be washed with an acidic aqueous solution such as of nitric acid, a basic aqueous solution such as of ammonia water, or an organic solvent such as an alcohol. When an aqueous nitric acid solution, for example, is used for this preparatory washing, it is commendable to repeat an operation of heating the carrier under normal pressure at 90° C. In this case, the catalyst which has undergone this operation must be washed with water. During this washing with water, however, the carrier is not always required to heat under normal pressure at 90° C.

The means for washing the carrier does not need to be particularly restricted. The carrier may be washed by being heated in conjunction with a washing liquid or by being exposed to a reduced pressure or increased pressure.

The catalyst which excels in catalytic qualities for the acrylic acid production can be obtained by washing the carrier preferably with water as described above or using the carrier exhibiting specific resistance of not less than 10,000 $\Omega$.cm (25° C.) for the water after the treatment mentioned above.

The catalyst for producing acrylic acid according to this invention can be prepared in accordance with the method known to the art except that the carrier described above is used instead. Specifically, the composition of catalyst, the method for preparation, the kind of carrier, and the method for supporting of a catalyst component on the carrier may be each any of those known to the art.

In the method for the preparation of the catalyst, the metal compounds to be used do not need to be limited to ammonium salts and nitrates but may be selected from among various oxides, carbonates, chlorides, sulfates, hydroxides, organic acid salts etc.

The amount of the catalytic component to be supported is not particularly limited but is only required to be such that the produced catalyst permits effective production of acrylic acid by gas phase partial oxidation of acrolein. This amount, for example, is in the range of 1–200 wt. %, preferably 10–100 wt. %, based on the weight of the carrier for producing acrylic acid.

The production of acrylic acid by the gas phase partial oxidation of acrolein or an acrolein-containing gas in the presence of the catalyst of this invention has no particular restriction. It can be effected by any of the methods which can be used for reactions of this kind and which are popularly known as usable therefor. The production, for example, only requires acrolein or an acrolein-containing gas to contact with the catalyst at a temperature in the range of 180–350° C., preferably 200–330° C., under normal pressure or by application of pressure.

(II) Organic Acid Anhydride or Nitril Compounds

This invention concerns a catalyst for the gas phase partial oxidation of an aromatic compound or an alkyl-substituted heterocyclic compound having a catalytically active component supported on an inert carrier, characterized by the carrier used therefor causing the water after undergoing the treatment mentioned above to exhibit specific resistance of not less than 20,000 $\Omega$.cm (25° C.).

This invention concerns a catalyst for the gas phase partial oxidation of an aromatic compound or an alkyl-substituted heterocyclic compound, a method for the preparation thereof, a method for the gas phase partial oxidation of an aromatic compound or an alkyl-substituted heterocyclic compound and more particularly concerns a catalyst suitable for the production of phthalic anhydride, maleic anhydride, pyromellitic anhydride, or aromatic nitrile (or heterocyclic nitrile) by the gas phase partial oxidation (or ammoxidation) respectively of orthoxylene (and/or naphthalene), benzene, 1,2,4,5-tetraalkyl benzene, or alkyl-substituted benzene derivative (or alkyl-substituted heterocyclic compound), a method for the preparation thereof, and a method for the gas phase partial oxidation of an aromatic compound or an alkyl-substituted heterocyclic compound by the use of the catalyst.

The inert carrier to be used in this invention does not need to discriminate the material itself to be used therefor. It may be any of the carriers which are popularly used and are known to be used in preparing catalysts for the gas phase partial oxidation of an aromatic hydrocarbon such as, for example, the production of phthalic anhydride by the gas phase partial oxidation of orthoxylene and/or naphthalene, the production of maleic anhydride by the gas phase partial oxidation of benzene, the production of pyromellitic anhydride by the gas phase partial oxidation of 1,2,4,5-tetraalkyl benzene, or the production of aromatic nitrile or heterocyclic nitrile by gas phase the ammoxidation of an alkyl-substituted benzene derivative or alkyl-substituted heterocyclic compound. As examples of the material which is popularly used for the carrier of catalyst, it may be cited, for example, alumina, silica, silica.alumina, titania, magnesia, silica.magnesia, silica.magnesia.alumina, silicon carbide, silicon nitride, and zeolite.

It is commonly used the inert carrier formed solely of silicon carbide or the inert carrier formed mainly of silicon carbide among other materials cited above. For example, JP-A-57-105,241 discloses a self-sintered silicon carbide being used as the carrier for a catalyst for the production of phthalic anhydride from orthoxylene and/or naphthalene, U.S. Pat. No. 4,760,153 discloses production of maleic anhydride from benzene with a catalyst in which a catalytically active component is supported on a self-sintered silicon carbide, U.S. Pat. No. 4,665,200 discloses use of a catalyst having a catalytically active component supported on a self-sintered silicon carbide as the catalyst for the production of pyromellitic anhydride from 1,2,4,5-tetramethyl benzene, and U.S. Pat. No. 4,939,260 discloses use of self-sintered silicon carbide as a carrier of the catalyst for producing benzonitrile from toluene. Further, JP-A-09-85,096 discloses an inert carrier formed by using silicon carbide in conjunction with silicon dioxide and mullite as inorganic binding agents.

The inert carrier which is the self-sintered silicon carbide mentioned above and the inert carrier having silicon carbide as a main component thereof are used advantageously in this invention. In these inert carriers, the latter carrier is particularly advantageously used because it is inexpensive, exhibits excellent thermal conductivity based on silicon carbide, and is easily molded in a required shape.

The expression "inert carrier having silicon carbide as a main component thereof" herein means a carrier of the type obtained by using silicon carbide as a main component, mixing it with an inorganic binding agent, and sintering the resultant mixture in the required shape. The silicon carbide content of the carrier is preferred to be not less than 70 wt. %. As an example of the carrier having silicon carbide as a main component thereof, it may be cited the inert carrier which, as disclosed in JP-A-09-85,096, has a silicon carbide content of not less than 70 wt. % and contains silicon dioxide and mullite as the inorganic binding agents.

Besides, an inert carrier that has steatite as a main component thereof is advantageously used in this invention.

As for the carrier to be used in this invention, physical properties, shape or size is not limited. As concerns physical properties, the specific surface area thereof may be not more than 0.3 m$^2$/g and preferably in the range of 0.02–0.2 m$^2$/g and the porosity thereof may be in the range of 0–35%, preferably 16–30%. The shape may be freely selected from among sphere, cylinder, hollow cylinder etc. As regards the size, the average particle diameter may be in the approximate range of 2–15 mm, preferably in the approximate range of 3–12 mm, in the case of spheres.

This invention is characterized by the carrier used therein causing the water after undergoing the treatment mentioned above to exhibit specific resistance of not less than 20,000 Ω.cm (25°). To be specific, the carrier to be used is such that when 300 ml of the carrier is placed in a conical beaker having an inner volume of 500 ml and dried at 120° C. for two hours, and then the dried carrier and (amount of water absorption+220) ml of purified water added thereto are heated at 90° C. under normal pressure for 30 minutes, the water subsequently to this treatment exhibits specific resistance not less than 2×10$^4$ Ω.cm (25° C.), preferably falling in the range of 25,000–1×10$^6$ Ω.cm (25° C.), and particularly preferably falling in the range of 3×10$^4$–1×10$^6$ Ω.cm (° C.).

The term "specific resistance" herein refers to the magnitude which is the reciprocal of the conductivity of water determined after the treatment mentioned above at 25° C. with a conductivity meter. In this invention, when the specific resistance is 20,000 Ω.cm, for example, it is expressed as 20,000 Ω.cm (25° C.).

The carrier which exhibits the specific resistance of not less than 20,000 Ω.cm (25° C.) for the water after the treatment mentioned above can be advantageously prepared by washing a given carrier with water, preferably purified water, to a certain level.

One concrete method for effecting this washing consists in that the specific resistance for the water after the treatment mentioned above exceeds 2×10$^4$ Ω.cm (25° C.), preferably falls in the range of 25,000 to 1×10$^6$ Ω.cm (25° C.), and more preferably 30,000–1×10$^6$ Ω.cm (25° C.), for example by repeating an operation of heating a carrier under normal pressure at 90° C. for 30 minutes. This operation does not need to be repeated when the first round of the operation allows the specific resistance for the water after the treatment mentioned above reaches a level exceeding 20,000 Ω.cm (25° C.). When this operation is performed up to a plurality of repetitions, each operation must use newly supplied water and require this water to be tested for specific resistance subsequently to the treatment mentioned above. The amount of water to be used for the washing does not need to be particularly limited. When the carrier has a volume of 300 ml, for example, the amount of water to be used is the sum of amount of water absorption+220 ml in the first round of the operation and 220 ml each in the second and subsequent rounds.

Prior to the washing with water described above, the carrier may be washed with an acidic aqueous solution such as of nitric acid, a basic aqueous solution such as of ammonia water, or an organic solvent such as an alcohol. When an aqueous nitric acid solution, for example, is used for this preparatory washing, it is commendable to repeat an operation of heating the carrier under normal pressure at 90° C. In this case, a carrier which has undergone this operation must be washed with water. During this washing with water, however, the carrier is not always required to be heat under normal pressure at 90° C.

The means suitable for washing the carrier are not particularly restricted. The carrier may be washed by being heated in conjunction with a washing liquid or by being exposed to a reduced pressure or increased pressure.

The catalyst of excellent catalytic properties for the gas phase partial oxidation of an aromatic compound or an alkyl-substituted heterocyclic compound can be obtained by washing the carrier preferably with water as described above or using the carrier exhibiting the specific resistance of not less than 20,000 Ω.cm (25° C.) for the water after the treatment mentioned above.

The catalyst of this invention for the gas phase partial oxidation of an aromatic compound or an alkyl-substituted heterocyclic compound can be prepared in accordance with the method known to the art except that the inert carrier mentioned above is used therefor.

The catalyst of this invention for the gas phase partial oxidation of an aromatic compound or an alkyl-substituted heterocyclic compound can be used for the gas phase partial oxidation of a varying an aromatic compound or an alkyl-substituted heterocyclic compound, typically for <1> the production of phthalic anhydride by the gas phase partial oxidation of orthoxylene and/or naphthalene, <2> the production of maleic anhydride by the gas phase partial oxidation of benzene, <3> the production of pyromellitic anhydride by the gas phase partial oxidation of 1,2,4,5-tetraalkyl benzene, and <4> the production of aromatic nitrile or heterocyclic nitrile by the gas phase ammoxidation of an alkyl-substituted benzene derivative or an alkyl-substituted heterocyclic compound. Incidentally, the term "gas phase partial oxidation" herein embraces gas phase ammoxidation.

Now, the items <1>–<4> mentioned above will be described in detail below.

<1> Production of Phthalic Anhydride From Orthoxylene and/or Naphthalene

Generally, it is used a catalyst in which a catalytically active component containing the oxides of (1) vanadium and (2) titanium is supported on the inert carrier mentioned above.

Particularly, catalysts suitable therefor are obtained by preparing an oxide composition containing (1) vanadium, (2) titanium, and (3) at least one element selected from the group consisting of alkali metal elements, rare earth elements, sulfur, phosphorus, antimony, niobium, and boron as a catalytically active component and supporting this oxide composition on the inert carrier mentioned above.

<2> Production of Maleic Anhydride From Benzene

Generally, it is used a catalyst in which a catalytically active component containing the oxides of (1) vanadium and (2) molybdenum is supported on the inert carrier mentioned above.

Particularly, catalysts suitable therefor are obtained by preparing an oxide composition containing (1) vanadium, (2) molybdenum, (3) phosphorus, and (4) at least one element selected from the group consisting of alkali metal elements, alkaline earth metal elements, and thallium as a catalytically active component and supporting this oxide composition on the carrier.

<3> Production of Pyromellitic Anhydride From 1,2,4,5-tetraalkyl Benzene

Generally, it is used a catalyst in which a catalytically active component containing vanadium oxide is supported on the inert carrier mentioned above.

Particularly, catalysts suitable therefor are obtained by preparing an oxide composition containing at least one element selected from the group consisting of phosphorus, molybdenum, tungsten, antimony, silver, boron, chromium, cerium, niobium, sulfur, alkali metal elements, alkaline earth metal elements, thallium, titanium, zirconium and tin besides vanadium as a catalytically active component and supporting this oxide composition on the carrier.

<4> Production of Aromatic Nitrile or Heterocyclic Nitrile from Alkyl-substituted Benzene Derivative or Alkyl-substituted Heterocyclic Compound by Ammoxidation Generally, it is used a catalyst in which a catalytically active component containing vanadium oxide is supported on the inert carrier mentioned above.

Particularly, catalysts suitable therefor are obtained by preparing an oxide composition containing (1) vanadium, (2) at least one oxide selected from the group consisting of titanium oxide, silicon oxide, alumina, diatomaceous earth, titanium-silicon complex oxide, titanium-zirconium complex oxide, and titanium-silicon-zirconium complex oxide, and (3) at least one element selected from the group consisting of molybdenum, tungsten, chromium, antimony, bismuth, phosphorus, niobium, iron, cobalt, nickel, manganese, and copper as a catalytically active component and supporting this oxide composition on the carrier.

As typical examples of the production of aromatic nitrile from an alkyl-substituted benzene derivative, the production of benzonitrile from toluene, ethyl benzene, n-propyl benzene, or cumene, the production of phthalonitrile from o-xylene, the production of isophthalonitrile from m-xylene, the production of terephthalonitrile from p-xylene, and the production of cyano anisole from methyl anisole may be cited. Among other productions mentioned above, the production of benzonitrile from toluene proves particularly advantageous. As typical examples of the production of heterocyclic nitrile from an alkyl-substituted heterocyclic compound, it may be cited, for example, the production of picolino-nitrile from α-picoline, the production of nicotino-nitrile from β-picoline, and the production of isonicotino-nitrile from γ-picoline.

Methods suitable for supporting the catalytically active substance on the inert carrier are not particularly restricted. It may be cited a method which comprises placing a prescribed amount of the inert carrier in a rotary drum capable of being externally heated and keeping the inert carrier at 200–300° C. and meanwhile spraying thereon a liquid (slurry) containing the catalytically active substance thereby supporting the active substance on the carrier. In this case, the amount of the active substance to be supported on the inert carrier depends on the size and the shape thereof. When the inert carrier is in the shape of spheres or cylinders, this amount may be proper in the range of 3–30 g, particularly 5–20 g of active substance/100 ml of inert carrier.

The reaction of gas phase partial oxidation contemplated by this invention can be effected in accordance with any of the methods popularly practiced in executing various reactions except that the catalyst for gas phase partial oxidation described above is adopted. Generally, it is carried out with a reaction tube made of carbon steel or stainless steel and loaded with the catalyst for gas phase partial oxidation of this invention. The reaction tube is preferred to keep at a constant temperature by means of a thermal medium such as molten salt so that the reaction temperature may be adjusted at a constant level by the removal of the heat of reaction. Conditions suitable for the reaction of gas phase partial oxidation are not particularly restricted. The reaction can be carried out under any of the conditions popularly adopted for varying reactions. In the case of the reaction <1> mentioned above, for example, it may bring the orthoxylene-containing gas into contact with the partial oxidation catalyst at a temperature in the range of 300–400° C., preferably 330–380° C., under normal pressure or by application of pressure.

EXAMPLE

Now, this invention will be described more specifically below with reference to examples. The conductivity was measured with a conductivity meter (available from Horiba K.K. in Japan as a type of "DS-12").

Example I-1

Three liters of a silica-alumina carrier (spheres, 3/16 inch in diameter, packing density 1.20 g/ml, and water absorption ratio 20%) was heated in three liters of purified water at 90° C. for 30 minutes to wash.

676 g of Ammonium molybdate, 149 g of ammonium metavanadate, 215 g of ammonium paratungstate and 3,500 ml of water were mixed and heated with stirring to dissolve. Separately, 154 g of copper nitrate was dissolved in 200 ml of water while the water was heating and stirring. The two aqueous solutions consequently obtained were mixed and placed in a ceramic evaporation dish held on a water bath. The mixed aqueous solution and two liters of the washed carrier dried thoroughly at 120° C. were together stirred in the dish and the catalyst component was supported on the carrier by means of evaporation and solidification. The resultant composite was heat-treated under a stream of air at 400° C. for six hours to obtain a catalyst 1. The metal element composition of this catalyst excepting oxygen was as follows:

$$Mo_{12}V_4W_{2.5}CU_2.$$

In a conical beaker, 500 ml in inner volume (based on JIS R-3503), 300 ml of the remaining washed carrier was placed and dried at 120° C. for two hours and the dried carrier and 292 ml [=(300×1.20×0.2)+220] of purified water added thereto were heated under normal pressure at 90° C. for 30 minutes. After treatment, the water was separated from the beaker and tested for conductivity. As a result, the water had a specific resistance of 16,300 Ω.cm (25° C.).

Example I-2

Three liters of the same carrier as used in Example I-1 and 3 liters of purified water added thereto were heated together at 90° C. for 30 minutes to wash the carrier. After treatment, the water was separated from the beaker. Two liters of purified water were newly added in the same beaker and the above same treatment was repeated to wash the carrier.

The procedure of Example I-1 was repeated except that the carrier washed twice was used instead to obtain a catalyst 2.

The conductivity was measured in the same manner as used in Example I-1, and as a result, the water had a specific resistance of 23,100 Ω.cm (25° C.).

Example I-3

Three liters of the same carrier as used in Example I-1 and 3 liters of purified water added thereto were heated together at 90° C. for 30 minutes to wash the carrier. After treatment, the water was separated from the beaker. Two liters of purified water were newly added in the same beaker and the above same treatment was repeated to wash the carrier. This operation was repeated once more.

676 g of Ammonium molybdate, 149 g of ammonium metavanadate, 215 g of ammonium paratungstate and 3,500 ml of water were mixed and heated with stirring to dissolve. Separately, 154 g of copper nitrate and 200 ml of water were mixed and heated with stirring to dissolve. The two aqueous solutions consequently obtained were mixed and evaporated and solidified while heating and stirring. The resultant blocks were dried in a drier at 120° C. for five hours and then pulverized to about 100 meshes of a powder. In a centrifugal flow coating apparatus, 2 liters of the washed carrier thoroughly dried in advance at 120° C. was placed and subsequently the aforementioned powder was thrown in together with distilled water as a binding agent while hot air at 90° C. was blown in order to support the catalyst components on the carrier. The spherical particles thus obtained were heat-treated under a stream of air at 400° C. for six hours to obtain a catalyst 3.

The conductivity was measured in the same manner as used in Example I-1, and as a result, the water had a specific resistance of 24,700 $\Omega$.cm (25° C.).

Example I-4

Three liters of the same carrier as used in Example I-1 and 3 liters of an aqueous nitric acid solution (2 mols/liter) added thereto were heated together under normal pressure at 90° C. for 30 minutes to wash the carrier. After treatment, the nitric acid solution was separated from the beaker. Two liters of purified water were newly added in the same beaker and the above same treatment was repeated to wash the carrier. This operation was repeated once more.

The procedure of Example I-1 was repeated except that the carrier washed mentioned above was used instead to obtain a catalyst 4.

The conductivity was measured in the same manner as used in Example I-1, and as a result, the water had a specific resistance of 21,600 $\Omega$.cm (25° C.).

Comparative Example I-1

As for the raw carrier not washed as used in Example I-1, the conductivity was measured in the same manner as used in Example I-1, and as a result, the water had a specific resistance of 8,500 $\Omega$.cm (25° C.).

The procedure of Example I-1 was repeated except that the carrier not washed mentioned above was used instead to obtain a catalyst 5.

Example I-5

Three liters of a steatite carrier (spheres, 3/16 inch in diameter, packing density 1.30 g/ml, and water absorption ratio 5%) and three liters of purified water were heated at 90° C. for 30 minutes. Then, the water was separated and then the remaining carrier and 2 liters of newly added purified water were heated together at 90° C. for 30 minutes to wash the carrier. This operation was repeated once more.

The procedure of Example I-1 was repeated except that the washed carrier mentioned above was used instead to obtain a catalyst 6.

In a conical beaker, 500 ml in inner volume, 300 ml of the remaining carrier was placed and dried at 120° C. for two hours. Then, the dried carrier and 240 ml [=(300×1.30×0.05)+220] of purified water added thereto were heated together under normal pressure at 90° C. for 30 minutes. After treatment, the water was separated from the beaker and tested for conductivity. As a result, the water had a specific resistance of 20,600 $\Omega$.cm (25° C.).

Example I-6

Three liters of the same carrier as used in Example I-5 and 3 liters of ammonia water (ammonia content 29%) added thereto were heated together under normal pressure at 90° C. for 30 minutes. Then, the ammonia water was removed and then the remaining carrier and 2 liters of newly added purified water were heated together at 90° C. for 30 minutes to wash the carrier. This operation was repeated once more.

The procedure of Example I-3 was repeated except that the washed carrier mentioned above was used instead to obtain a catalyst 7.

The conductivity was measured in the same manner as used in Example I-5, and as a result, the water had a specific resistance of 13,300 $\Omega$.cm (25° C.).

Comparative Example I-2

As for the raw carrier not washed as used in Example I-5, the conductivity was measured in the same manner as used in Example I-5, and as a result, the water had a specific resistance of 7,900 $\Omega$.cm (25° C.).

The procedure of Example I-1 was repeated except that the carrier not washed mentioned above was used instead to obtain a catalyst 8.

Example I-7

Three liters of a titania-zirconia carrier (3/16-inch spheres, packing density 1.0 g/ml, and water absorption ratio 30%) was heated in three liters of purified water at 90° C. for 30 minutes to wash. Then, the water was separated and then the remaining carrier and 2 liters of newly added purified water were heated together at 90° C. for 30 minutes to wash the carrier. This operation was repeated once more.

The procedure of Example I-1 was repeated except that the washed carrier mentioned above was used instead to obtain a catalyst 9.

In a conical beaker, 500 ml in inner volume, 300 ml of the washed carrier was placed and dried at 120° C. for two hours. Then, the dried carrier and 310 ml [=(300×1.0×0.3)+220] of purified water added thereto were heated together under normal pressure at 90° C. for 30 minutes. After treatment, the water was separated from the beaker and tested for conductivity. As a result, the water had a specific resistance of 11,900 $\Omega$.cm (25° C.).

Comparative Example I-3

As for the raw carrier not washed as used in Example I-7, the conductivity was measured in the same manner as used in Example I-7, and as a result, the water had a specific resistance of 9,000 $\Omega$.cm (25° C.).

The procedure of Example I-1 was repeated except that the carrier not washed mentioned above was used instead to obtain a catalyst 10.

Example I-8

In a U-shaped stainless steel tube, 25 mm in inside diameter, 500 ml of each catalyst (catalyst 1–catalyst 10) obtained in Examples I-1 to I-7 and Comparative Examples I-1 to I-3 respectively was loaded, a reaction gas of the following composition was then introduced to the catalyst bed at a space velocity (SV) of 2,000 $Hr^{-1}$ and allowed to react:

| | |
|---|---|
| Acrolein | 5 vol. % |
| Air | 25 vol. % |
| Steam | 20 vol. % |
| Nitrogen | 50 vol. %. |

The results are shown in Table I-1.

TABLE I-1

| Example I- | Catalyst No. | Carrier (oxide) | Washing method | SRW (Ωcm) | BTN (° C.) | AC (mol %) | OPYA (mol %) | SAA (mol %) |
|---|---|---|---|---|---|---|---|---|
| 1 | Cat. 1 | Si-Al | One time | 16300 | 250 | 98.9 | 93.7 | 94.7 |
| 2 | Cat. 2 | Si-Al | Two times | 23100 | 250 | 99.1 | 93.9 | 94.8 |
| 3 | Cat. 3 | Si-Al | Three times | 24700 | 250 | 99.5 | 94.9 | 95.4 |
| 4 | Cat. 4 | Si-Al | HNO$_3$ | 21600 | 250 | 98.9 | 93.3 | 94.3 |
| C. Ex. I-1 | Cat. 5 | Si-Al | None | 8500 | 250 | 97.4 | 91.1 | 93.5 |
| 5 | Cat. 6 | Steatite | Three times | 20600 | 250 | 99.4 | 94.3 | 94.9 |
| 6 | Cat. 7 | Steatite | Ammonia water | 13300 | 250 | 99.4 | 95.1 | 95.7 |
| C. Ex. I-2 | Cat. 8 | Steatite | None | 7900 | 250 | 97.8 | 92.2 | 94.3 |
| 7 | Cat. 9 | Ti-Zr | Three times | 11900 | 250 | 98.5 | 93.0 | 94.4 |
| C. Ex. I-3 | Cat. 10 | Ti-Zr | None | 9000 | 250 | 97.3 | 91.5 | 94.0 |

SRW: Specific resistance of water;
BTN: Bath temp. of nitrate salt;
AC: Acrolein Conversion;
OPYA: One path yield of acrylic acid;
SAA: Selectivity of acrylic acid;
Si-Al: Silica-alumina;
Ti-Zr: Titania-Zirconia;
C. Ex.: Comparative Example

Example I-9

The catalysts (catalyst 1 and catalyst 5) obtained in Example I-1 and Comparative Example I-1 respectively were each made to react under the conditions described in Example I-8. This reaction was carried out continuously for 4,000 hours. The results are shown in Table I-2.

TABLE I-2

| Example I- | Catalyst No. | Carrier (oxide) | Washing method | SRW (Ωcm) | BTN (° C.) | RT (hrs) | AC (mol %) | OPYA (mol %) | SAA (mol %) |
|---|---|---|---|---|---|---|---|---|---|
| 1 | Cat. 1 | Si-Al | One time | 16300 | 250 | Initial | 98.9 | 93.7 | 94.7 |
| | | | | | 250 | 4000 | 98.5 | 93.1 | 94.5 |
| C. Ex. I-1 | Cat. 5 | Si-Al | None | 8500 | 250 | Initial | 97.4 | 91.1 | 93.5 |
| | | | | | 250 | 4000 | 95.8 | 89.6 | 93.5 |

SRW: Specific resistance of water;
BTN: Bath temp. of nitrate salt;
RT: Reaction time;
AC: Acrolein Conversion;
OPYA: One path yield of acrylic acid;
SAA: Selectivity of acrylic acid;
Si-Al: Silica-alumina;
Ti-Zr: Titania-Zirconia;
C. Ex.: Comparative Example

Example II-1

Washing of Carrier (1)

Three liters of hollow cylinder of carrier (1) were heated in three liters of purified water at 90° C. for 30 minutes to wash, the carrier (1) consisting of silicon carbide, silicon dioxide, and mullite at a weight percentage of 90:5:5, containing an alkali metal element and an alkaline earth metal element in a total of 0.2 wt. % (hereinafter referred to as "alkali content"), and exhibiting a packing density of 0.88 g/ml, a water absorption ratio of 15%, a specific surface area of 0.14 m$^2$/g, and a porosity of 23%, each hollow cylinder measuring 6.9 mm in outside diameter, 3.7 mm in inside diameter, and 7.3 mm in length. The washed carrier is labeled as (1W).

In a conical beaker, 500 ml in inner volume (based on JIS R-3503), 300 ml of the carrier (1W) was dried at 120° C. for two hours and then the dried carrier and 260 ml [=(300× 0.88×0.15)+220] of purified water added thereto were heated together under normal pressure at 90° C. for 30 minutes. After treatment, the water was separated from the beaker and tested for conductivity. As a result, the water had a specific resistance of 27,400 Ω.cm (25° C.).

Preparation of Catalyst

Ilmenite was mixed with 80% concentrated sulfuric acid, the mixture was allowed to react thoroughly and then diluted with water to give an aqueous solution containing titanium sulfate. The resultant aqueous solution was added with an iron piece as a reducing agent, heated in order to reduce the iron component in the ilmenite into ferrous ions and cooled to induce precipitation and separation of ferrous sulfate. To the resultant aqueous titanium sulfate solution, steam heated to 150° C. was brown to induce sedimentation of hydrated titanium oxide. This sediment was washed with water, washed with acid, given a secondary washing with water, and then calcined at a temperature of 800° C. under a stream of air for four hours. The calcined product was pulverized with a jet stream of air to obtain anatase titanium dioxide having an average particle diameter of 0.5 μm and a specific surface area of 22 m$^2$/g.

Separately, an aqueous oxalic acid solution was obtained by dissolving 100 g of oxalic acid into 3200 ml of deionized water. In the aqueous solution, 23.63 g of ammonium metavanadate, 2.99 g of ammonium dihydrogen phosphate, 9.40 g of niobium chloride, 4.13 g of cerium sulfate, and 18.35 g of antimony trioxide were placed and thoroughly stirred. The solution thus obtained and 900 g of the aforementioned anatase titanium dioxide added thereto were stirred together with an emulsifying machine to prepare a catalyst slurry.

In a stainless steel rotary kiln measuring 35 cm in diameter and 80 cm in length and adapted to be externally heated, 1000 ml of the carrier (1W) was placed and preheated to 200–250° C. and, with the kiln kept in rotation, the aforementioned catalyst slurry was sprayed onto the preheated carrier to support the catalytically active substance at a ratio of 9.5 g/100 ml of the carrier. The resultant composite was calcined under a stream of air at 580° C. for 6 hours to prepare a catalyst (A).

The procedure for the preparation of catalyst (A) was repeated except that the amount of ammonium dihydrogen phosphate was changed to 11.96 g to prepare a catalyst (B).

The catalyst compositions of catalyst (A) and catalyst (B) are shown in Table II-1 below.

Partial Oxidation

In a carbon steel reaction tube, 25 mm in inside diameter and 3 m in length, immersed in a molten salt bath retained at a temperature of 350° C., firstly catalyst (B) was loaded to a height of 1 m in the feed gas outlet part as a second-stage catalyst and then catalyst (A) was piled on the loaded catalyst (B) to a height of 1.8 m in the inlet part as first-stage catalyst.

A feed gas obtained by mixing orthoxylene and air at a ratio of 70 g/Nm$^3$ (air) was introduced into the reactor through the upper inlet at a space velocity (SV) of 2910 Hr$^{-1}$ (STP: Standard Temperature and Pressure) to effect partial oxidation of orthoxylene. The yield of phthalic anhydride and the amount of phthalide (by-product) were measured during the initial stage of reaction and three months after the start of the reaction.

The results are shown in Table II-2 below. The conversion of orthoxylene was nearly 100%, a fact which implies that the yield mentioned above could be regarded as the selectivity of phthalic anhydride.

Example II-2

The procedure of Example II-1 (preparation of catalyst) was repeated except that a carrier (2W) was used instead of carrier (1W) to prepare catalysts (C) and (D) respectively.

The procedure of Example II-1 (Partial oxidation) was repeated except that catalysts (C) and (D) were used instead of catalysts (A) and (B).

The compositions of catalysts (C) and (D) are shown in Table II-1 below and the results of the reaction of partial oxidation are shown in Table II-2 below.

Washing of Carrier (2)

Three liters of hollow cylinder of steatite carrier (2) were heated in 3 liters of purified water at 90° C. for 30 minutes, the steatite carrier (2) exhibiting a loaded density of 1.08 g/ml, a water absorption ratio of 3%, a specific surface area of 0.007 m$^2$/g, and a porosity of 5%, each hollow cylinder measuring 6.9 mm in outside diameter, 3.8 mm in inside diameter, and 7.0 mm in length. The washed carrier was labeled as (2W).

In a conical beaker, 500 ml in inner volume, 300 ml of the carrier (2W) was dried at 120° C. for two hours and then the dried carrier and 230 ml [=(300×1.08×0.03)+220] of purified water added thereto were heated together under normal pressure at 90° C. for 30 minutes. After treatment, the water was separated from the beaker and tested for conductivity. As a result, the water had a specific resistance of 44,200 Ω.cm (25° C.).

Comparative Example II-1

The procedure of Example II-1 (preparation of catalyst) was repeated except that the raw carrier (1) not washed as indicated in Example II-1 was used instead of carrier (1W) to prepare catalysts (E) and (F) respectively.

The procedure of Example II-1 (Partial oxidation) was repeated except that catalysts (E) and (F) were used instead of catalysts (A) and (B).

The compositions of catalysts (E) and (F) are shown in Table II-1 below and the results of the reaction of partial oxidation are shown in Table II-2 below.

In a conical beaker, 500 ml in inner volume, 300 ml of the carrier (1) was dried at 120° C. for two hours and the dried carrier and 260 ml [=(300×0.88×0.15)+220] of purified water added thereto were heated together under normal pressure at 90° C. for 30 minutes. After treatment, the water was separated from the beaker and tested for conductivity. As a result, the water had a specific resistance of 10,500 Ω.cm (25° C.).

Comparative Example II-2

The procedure of Example II-2 (preparation of catalyst) was repeated except that the raw carrier (2) not washed as indicated in Example II-2 was used instead of carrier (2W) to prepare catalysts (G) and (H) respectively.

The procedure of Example II-2 (Partial oxidation) was repeated except that catalysts (G) and (H) were used instead of catalysts (C) and (D).

The compositions of catalysts (G) and (H) are shown in Table II-1 below and the results of the reaction of partial oxidation are shown in Table II-2 below.

In a conical beaker, 500 ml in inner volume, 300 ml of the carrier (2) was dried at 120° C. for two hours and the dried carrier and 230 ml [=(300×1.08×0.03)+220] of purified water added thereto were heated together under normal pressure at 90° C. for 30 minutes. After treatment, the water was separated from the beaker and tested for conductivity. As a result, the water had a specific resistance of 9,500 Ω.cm (25° C.)

TABLE II-1

| Example II- | Carrier Name | SRW | Cata-lyst | Cata-lyst bed | Composition of catalyst active components (wt. ratio) | | | | | |
|---|---|---|---|---|---|---|---|---|---|---|
| | | | | | $V_2O_5$ | $TiO_2$ | $Nb_2O_5$ | $P_2O_5$ | $Cs_2O$ | $Sb_2O_3$ |
| 1 | 1W | 27,400 | A | First | 2 | 98 | 0.5 | 0.2 | 0.35 | 2.0 |
| | 1W | 27,400 | B | Second | 2 | 98 | 0.5 | 0.8 | 0.35 | 2.0 |
| 2 | 2W | 44,200 | C | First | 2 | 98 | 0.5 | 0.2 | 0.35 | 2.0 |
| | 2W | 44,200 | D | Second | 2 | 98 | 0.5 | 0.8 | 0.35 | 2.0 |
| C. Ex II-1 | 1 | 10,500 | E | First | 2 | 98 | 0.5 | 0.2 | 0.35 | 2.0 |
| | 1 | 10,500 | F | Second | 2 | 98 | 0.5 | 0.8 | 0.35 | 2.0 |
| C. Ex XI-2 | 2 | 9,500 | G | First | 2 | 98 | 0.5 | 0.2 | 0.35 | 2.0 |
| | 2 | 9,500 | H | Second | 2 | 98 | 0.5 | 0.8 | 0.35 | 2.0 |

SRW: Specific resistance of water;
C. Ex.: Comparative Example

TABLE II-2

| | Initial stage of reaction | | | After three months | | |
|---|---|---|---|---|---|---|
| Example II- | RT (° C.) | YPA (wt %) | YPA (mol %) | RT (° C.) | YPA (wt %) | YPA (mol %) |
| 1 | 350 | 112.3 | 0.08 | 350 | 112.6 | 0.06 |
| 2 | 354 | 111.6 | 0.08 | 354 | 111.7 | 0.07 |
| C. Ex. II-1 | 353 | 110.5 | 0.08 | 353 | 109.5 | 0.20 |
| C. Ex. II-2 | 355 | 110.1 | 0.08 | 355 | 109.4 | 0.12 |

RT: Reaction temperature;
YPA: Yield of phthalic anhydride;
YP: Yield of phthalide Example II-3
Preparation of Catalyst In 1000 ml of purified water, 250 g of oxalic acid was dissolved. In the resultant aqueous solution, 235 g of ammonium metavanadate, 142 g of ammonium molybdate, 2.91 g of cesium sulfate, 7.45 g of sodium carbonate, 20.5 g of silver nitrate, and 4.62 g of ammonium dihydrogen phosphate were sequentially added with stirring.

In a stainless steel rotary kiln measuring 35 cm in diameter and 80 cm in length and adapted to be externally heated, 1.8 kg of the carrier (1W) was placed and preheated to 200–250° C. and, with the kiln kept in rotation, the aqueous solution was sprayed onto the preheated carrier to effect supporting of the catalytically active substance at a ratio of 18 g/100 ml of the carrier. The resultant composite was calcined under a reducing atmosphere at 500° C. for 8 hours to prepare a catalyst (I).

The procedure of catalyst (I) was repeated except that the amount of sodium carbonate was changed to 8.52 g and the amount of cesium sulfate was changed to 0.727 g respectively to prepare a catalyst (J).

The compositions of catalytically active components in catalysts (I) and (J) are shown in Table II-3 below.

Partial Oxidation

In a stainless steel reactor, 25 mm in inside diameter and 3.5 m in length, immersed in a molten salt bath, firstly catalyst (J) was loaded to a height of 1.5 m and then catalyst (I) was loaded thereon to a height of 1 m. To the catalyst beds thus formed, air was introduced at a space velocity (SV) of 1000 $Hr^{-1}$ and 0.3 vol. %, based on the introduced air, of benzene (benzene concentration of 10 $g/Nm^3$) was then introduced for 15 hours to effect activation of the catalysts.

Subsequently, as a steady-state reaction, a benzene-air mixed gas having a benzene concentration of 50 $g/Nm^3$ was introduced into the reactor through the upper part thereof under the conditions of a molten salt bath temperature of 365° C. and a space velocity (SV) of 2500 $Hr^{-1}$ to effect a reaction of partial oxidation.

The yield of maleic anhydride and the conversion of benzene were measured during the initial stage of the reaction and three months after the start of the reaction. The results are shown in Table II-4 below.

Comparative Example II-3

The procedure of Example II-3 (preparation of catalyst) was repeated except that the raw carrier (1) not washed as indicated in Example II-3 was used instead of carrier (1W) to prepare catalysts (K) and (L) respectively.

The procedure of Example II-3 (Partial oxidation) was repeated except that catalysts (K) and (L) were used instead of catalysts (I) and (J).

The compositions of catalysts (K) and (L) are shown in Table II-3 and the results of the reaction of partial oxidation are shown in Table II-4.

TABLE II-3

| Example II- | Carrier Name | SRW (Ωcm) | Cata-lyst | Cata-lyst bed | Composition of catalyst active components (mol ratio) | | | | | |
|---|---|---|---|---|---|---|---|---|---|---|
| | | | | | $V_2O_5$ | $MoO_3$ | $Na_2O$ | $P_2O_5$ | $Cs_2O$ | $Ag_2O$ |
| 3 | 1W | 27.400 | I | First | 1 | 0.8 | 0.07 | 0.02 | 0.008 | 0.06 |
| | 1W | 27.400 | J | Second | 1 | 0.8 | 0.08 | 0.02 | 0.002 | 0.06 |
| C. Ex. II-3 | 1 | 10.500 | K | First | 1 | 0.8 | 0.07 | 0.02 | 0.008 | 0.06 |
| | 1 | 10.500 | L | Second | 1 | 0.8 | 0.08 | 0.02 | 0.002 | 0.06 |

SRW: Specific resistance of water;
C. Ex.: Comparative Example

TABLE II-4

| Example II- | Initial stage of reaction | | | After three months | | |
|---|---|---|---|---|---|---|
| | RT (° C.) | YMA (wt %) | CB (%) | RT (° C.) | YMA (wt %) | CB (%) |
| 3 | 364 | 99.0 | 98.0 | 364 | 99.1 | 98.1 |
| C. Ex. II-3 | 367 | 97.1 | 98.0 | 367 | 95.8 | 96.7 |

RT: Reaction temperature;
YMA: Yield of maleic anhydride;
CB: Conversion of benzene;
C. Ex.: Comparative Example

Example II-4
Preparation of Catalyst

In 350 ml of deionized water, 56 g of oxalic acid was dissolved. In the resultant aqueous solution, 28 g of ammonium metavanadate was placed and dissolved. The mixed aqueous solution, 10.5 g of antimony trioxide and 239 g of anatase titanium dioxide having a specific surface area of 20 $m^2/g$ as determined by the BET (Brunauer-Emmet-Teller) method added thereto were uniformly mixed together and then the resultant mixture was diluted with deionized water to prepare about 900 ml of a catalyst slurry.

In a stainless steel rotary kiln measuring 35 cm in diameter and 80 cm in length and adapted to be externally heated, 900 g of the carrier (1W) was placed and preheated to 200–250° C. and, with the kiln kept in rotation, the slurry was sprayed onto the preheated carrier to effect supporting of a catalytically active substance at a ratio of 5 g per 100 g of the catalyst. The resultant composite was calcined under a stream of air at 550° C. for 6 hours to prepare a catalyst (M). The composition of catalyst (M) is shown in Table II-5 below.

Separately, 240 g of oxalic acid was dissolved in 700 ml of deionized water. The resultant aqueous solution, 120 g of ammonium metavanadate and 18.1 g of ammonium molybdate added thereto were uniformly mixed together. The produced mixture, 3.54 g of ammonium dihydrogen phosphate and 8.71 g of silver nitrate dissolved in a small amount of deionized water were uniformly mixed together. The resultant mixture was further mixed with 20 g of silicon carbide whiskers to prepare 900 ml of a catalyst slurry.

In a stainless steel rotary kiln measuring 35 cm in diameter and 80 cm in length and adapted to be externally heated, 900 g of the carrier (1W) was placed and preheated to 200–250° C. and, with the kiln kept in rotation, the slurry was sprayed onto the preheated carrier to effect supporting of a catalytically active substance at a ratio of 5 g per 100 g of the catalyst. The resultant composite was calcined under a stream of air at 500° C. for 6 hours to prepare a catalyst (N). The composition of catalyst (N) is shown in Table II-5 below.

Partial Oxidation

In a stainless steel reactor, 25 mm in inside diameter and 4 m in length, immersed in a molten salt bath kept at a temperature of 395° C., firstly catalyst (N) was loaded to a height of 1.7 m, then catalyst (M) diluted to ½.5 with a self-sintered silicon carbide carrier weighing 1.5 times as much as the catalyst loaded thereon to a height of 0.8 m and DENSTONE carrier having an average diameter of 8 mm (available from Norton Corp.) loaded further thereon to a height of 0.5 m.

A feed gas prepared by mixing a synthesis gas consisting of 21 vol. % of oxygen and 79 vol. % of nitrogen with Durene at a ratio of 30 $g/Nm^3$ (synthesis gas) was introduced into the reactor through the upper inlet at a space velocity (SV) of 6000 $Hr^{-1}$ (STP) to effect a reaction of partial oxidation of Durene.

The yield of pyromellitic anhydride was measured during the initial stage of reaction and three months after start of the reaction. The results are shown in Table II-6 below.

Incidentally, the conversion of Durene was 100%, a fact which implies that the yield mentioned above could be regarded as the selectivity of pyromellitic anhydride.

Comparative Example II-4

The procedure of Example II-4 (preparation of catalyst) was repeated except that the raw carrier (1) not washed as indicated in Example II-4 was used instead of carrier (1W) to prepare catalysts (O) and (P) respectively.

The procedure of Example II-4 (Partial oxidation) was repeated except that catalysts (O) and (P) were used instead of catalysts (M) and (N).

The compositions of catalysts (O) and (P) are shown in Table II-5 and the results of the reaction of partial oxidation are shown in Table II-6.

TABLE II-5

| Example II- | Carrier | | Cata-lyst | Cata-lyst bed | Composition of catalyst active components (mol ratio) | | | | | | | |
|---|---|---|---|---|---|---|---|---|---|---|---|---|
| | Name | SRW (Ωcm) | | | $V_2O_5$ | $TiO_2$ | $Sb_2O_4$ | $MoO_3$ | $P_2O_5$ | $Ag_2O$ | CaO | Whisker |
| 4 | 1W | 27,400 | M | First | 4 | 100 | 1.2 | — | — | — | — | — |
|  | 1W | 27,400 | N | Second | 1 | — | — | 0.20 | 0.30 | 0.1 | 0.04 | 5.1 |
| C. Ex. II-4 | 1 | 10,500 | O | First | 4 | 100 | 1.2 | — | — | — | — | — |
|  | 1 | 10,500 | P | Second | 1 | — | — | 0.20 | 0.30 | 0.1 | 0.04 | 5.1 |

SRW: Specific resistance of water;
C. Ex.: Comparative Example;
Whisker is calculated as wt. % among the catalyst active components.

TABLE II-6

| Example II- | Initial stage of reaction | | After three months | |
|---|---|---|---|---|
| | RT (° C.) | YPA (mol %) | RT (° C.) | YPA (mol %) |
| 4 | 398 | 67.6 | 398 | 67.3 |
| C. Ex. II-4 | 395 | 65.3 | 395 | 63.8 |

RT: Reaction temperature;
YPA: Yield of pyromellitic anhydride;
C. Ex.: Comparative Example

Example II-5
Washing of Carrier (3)

Three liters of spheres of carrier (3) were heated in three liters of purified water at 90° C. for 30 minutes, the carrier (3) consisting of silicon carbide, silicon dioxide, and mullite at a weight percentage of 90:5:5, having an alkali content of 0.2 wt. %, and exhibiting a packing density of 1.20 g/ml, a water absorption ratio of 15%, a specific surface area of 0.15 m$^2$/g, and a porosity of 26%, each sphere measuring 5 mm in diameter. The washed carrier is labeled as (3W).

In a conical beaker, 500 ml in inner volume, 300 ml of the carrier (3W) was dried at 120° C. for two hours and then the dried carrier and 274 ml [=(300×1.20×0.15)+220] of purified water added thereto were heated together under normal pressure at 90° C. for 30 minutes. After treatment, the water was separated from the beaker and tested for conductivity. As a result, the water had a specific resistance of 23,400 Ω.cm (25° C.).

Preparation of Catalyst

A complex oxide consisting of titanium and silicon was prepared by the method as follows. It was used, as titanium sources, an aqueous sulfuric acid solution of titanyl sulfate consisting of 250 g of $TiOSO_4$ per liter (as $TiO_2$) and the total of 1100 g of $H_2SO_4$ per liter. Separately, in 400 liters of water, 280 liters of ammonia water (25% $NH_3$) were added and 16.9 kg of silica sol containing about 30 wt. % of $SiO_2$ (available from Nissan Chemicals Industries, Ltd. in Japan, type "Snowtex NCS-30") were further added. To the solution consequently obtained, an aqueous titanium-containing sulfuric acid solution obtained by diluting 153 liters of the aqueous sulfuric acid solution of titanyl sulfate mentioned above with 300 liters of water, was gradually added dropwise with stirring to induce formation of coprecipitated gel. The solution containing the gel was left standing at rest for 15 hours. The $TiO_2$:$SiO_2$ gel thus obtained was separated by filtration, washed with water, and dried at 200° C. for 10 hours. Then, the dried gel was calcined in an atmosphere of air at 550° C. for six hours. The produced powder had a composition, $TiO_2$:$SiO_2$=85:15 (molar ratio), and a BET surface area of 180 m$^2$/g. The powder obtained here is labeled as TS-1. A catalytically active component was prepared from this powder by the method as follows.

An aqueous vanadium oxalate solution was prepared by dissolving 23.4 g of ammonium metavanadate in an aqueous oxalic acid solution. Separately, an aqueous antimony tartrate solution was made by dissolving 51 g of antimony trioxide into an aqueous solution of tartaric acid. The two aqueous solutions were mixed. The mixed aqueous solutions and 400 g of TS-1 added thereto were thoroughly mixed to obtain a slurry. This slurry was sprayed, till a supporting ratio of 10 wt. %, on 2 liters of the carrier (3W) heated in advance. Then, the resultant composite was calcined in a stream of air at 550° C. for five hours to prepare a catalyst (Q). The composition of catalyst (Q) is shown in Table II-7 below.

Reaction of Ammoxidation

The catalyst (Q) was loaded to a height of 4 m in a stainless steel reaction tube, 25 mm in inside diameter and 5 m in length, heated with a molten salt. A feed gas consisting of 3 vol. % of toluene, 6 vol. % of ammonia, 10 vol. % of oxygen, and 81 vol. % of nitrogen was introduced into the reaction tube from the upper part, passed therethrough at a space velocity of 900 Hr$^{-1}$ (STP) and allowed to induce a reaction at a temperature of 390° C. The yield of benzonitrile was measured during the first stage of the reaction and six months after the start of the reaction. The results are shown in Table II-8 below.

Comparative Example II-5

The procedure of Example II-5 (preparation of catalyst) was repeated except that the raw carrier (3) not washed as indicated in Example II-4 was used instead of carrier (3W) to prepare a catalyst (R).

The procedure of Example II-5 (ammoxidation) was repeated except that catalyst (R) was used instead of catalyst (Q).

The composition of catalyst (R) is shown in Table II-7 below and the results of the reaction of partial ammoxidation are shown in Table II-8 below.

In a conical beaker, 500 ml in inner volume, 300 ml of the carrier (3) was placed and dried at 120° C. for two hours and then the dried carrier and 274 ml [=(300×1.20×0.15)+220] of purified water added thereto were heated together under normal pressure at 90° C. for 30 minutes. After treatment, the water was separated from the beaker and tested for conductivity. As a result, the water had a specific resistance of 9,800 Ω.cm (25° C.).

While the embodiments or examples of the present invention, as herein disclosed, constitute a preferred form, it is to be understood that other form might be adopted.

TABLE II-7

| Example II- | Carrier | | Catalyst | Composition of catalyst active components (mol ratio) | | | |
|---|---|---|---|---|---|---|---|
| | Name | SRW (Ωcm) | | $V_2O_5$ | $Sb_2O_3$ | $TiO_2$ | $SiO_2$ |
| 5 | 3W | 23,400 | Q | 1 | 1.75 | 22.1 | 3.9 |
| C. Ex. II-5 | 3 | 9,800 | R | 1 | 1.75 | 22.1 | 3.9 |

SRW: Specific resistance of water;
C. Ex.: Comparative Example

TABLE II-8

| Example II- | Initial stage of reaction | | After six months | |
|---|---|---|---|---|
| | RT (° C.) | YB (mol %) | RT (° C.) | YB (mol %) |
| 5 | 389 | 87.6 | 390 | 87.5 |
| C. Ex. II-5 | 393 | 85.4 | 393 | 83.2 |

RT: Reaction temperature;
YB: Yield of benzonitrile;
C. Ex.: Comparative Example

What is claimed is:

1. A method for the production of a partially oxidized organic compound, which comprises effecting gas phase partial oxidation of an organic substrate or an organic substrate-containing gas with molecular oxygen or a molecular oxygen-containing gas in the presence of a catalyst including an inert carrier and a catalytically active component supported thereon, wherein the carrier is washed with water, with water and an aqueous acid solution, or with water and an aqueous ammonia solution, dried, exposed to additional water, and separated from the additional water, such that the additional water exhibits specific resistance of not less than 10,000 ohms.cm (25° C.) when the catalyst is used for producing an unsaturated aldehyde or unsaturated carboxylic acid of not less than three carbon atoms, or specific resistance of not less than 20,000 ohms.cm (25° C.) when the catalyst is used for producing an organic anhydride or nitrile compound of not less than four carbon atoms;

wherein the specific resistance is measured according to the following treatment: in a conical beaker having an inner volume of 500 mL, 300 mL of the carrier is placed inside and dried at 120° C. for two hours and then the dried carrier and an amount of purified water equal to the total of the "amount of water absorption" in mL plus 220 mL ("amount of water absorption"+ 220, mL) added thereto are heated together under normal pressure at 90° C. for 30 minutes, wherein the "amount of water absorption" is A/B in which A=300 (mL)×packing density (g/mL)×water absorption ratio (% by weight)/100, and B=density of water (g/mL).

2. A method according to claim 1, wherein the organic substrate is acrolein, the partially oxidized organic compound is acrylic acid and the additional water exhibits specific resistance of not less than 10,000 Ω.cm (25° C.).

3. A method according to claim 1, wherein the organic substrate is orthoxylene and/or naphthalene, the partially oxidized organic compound is phthalic anhydride and the additional water exhibits specific resistance of not less than 20,000 Ω.cm (25° C.).

4. A method according to claim 1, wherein the organic substrate is benzene, the partially oxidized organic compound is maleic anhydride and the additional water exhibits specific resistance of not less than 20,000 Ω.cm (25° C.).

5. A method according to claim 1, wherein the organic substrate is 1,2,4,5-tetraalkylbenzene, the partially oxidized organic compound is pyromellitic anhydride and the additional water exhibits specific resistance of not less than 20,000 Ω.cm (25° C.).

6. A method according to claim 1, wherein the organic substrate is an alkyl-substituted benzene, the partially oxidized organic compound is an aromatic nitrile and the additional water exhibits specific resistance of not less than 20,000 Ω.cm (25° C.).

7. A method according to claim 1, wherein the organic substrate precursor is an alkyl-substituted heterocyclic compound, the partially oxidized organic compound is a heterocyclic nitrile and the additional water exhibits specific resistance of not less than 20,000 Ω.cm (25° C.).

* * * * *